United States Patent [19]

Ono

[11] Patent Number: 5,061,447
[45] Date of Patent: Oct. 29, 1991

[54] CATALYTIC COMBUSTION TYPE CO GAS SENSOR

[76] Inventor: Yoshio Ono, No. 3865-1, Matsubushi, Matsubushi-machi, Kitakatsushika-gun, Saitama-ken, Japan

[21] Appl. No.: 389,540

[22] Filed: Aug. 4, 1989

[30] Foreign Application Priority Data

Sep. 14, 1988 [JP] Japan ............................... 63-231276
Sep. 21, 1988 [JP] Japan ............................... 63-234748

[51] Int. Cl.$^5$ ........................................... G01N 27/16
[52] U.S. Cl. ........................................ 422/96; 422/94; 422/95; 422/97; 436/134; 436/152; 73/23.21; 73/31.05; 324/706; 324/720
[58] Field of Search ............... 422/94, 95, 96, 98, 422/97; 436/134, 144, 152, 159, 160; 73/23.21, 25.03, 31.05; 340/633; 338/34; 324/706, 720

[56] References Cited

U.S. PATENT DOCUMENTS

| | | | | |
|---|---|---|---|---|
| 3,080,745 | 4/1960 | Jones | .................................. | 73/23.21 |
| 3,476,517 | 11/1969 | Smith | .................................. | 422/96 |
| 3,519,391 | 7/1970 | Winter et al. | .................................. | 436/152 |
| 3,533,858 | 10/1970 | Seibel et al. | .................................. | 73/25.03 |
| 4,072,467 | 2/1978 | Jones | .................................. | 422/97 |
| 4,123,225 | 10/1978 | Jones et al. | .................................. | 422/98 |
| 4,198,850 | 4/1980 | Firth et al. | .................................. | 73/31.05 |
| 4,305,724 | 12/1981 | Micko | .................................. | 422/94 |
| 4,777,826 | 10/1988 | Rud, Jr. et al. | .................................. | 73/766 |
| 4,854,155 | 8/1989 | Poli | .................................. | 73/31.05 |

FOREIGN PATENT DOCUMENTS 0004043 1/1981 Japan ................................... 422/97
1246660 11/1986 Japan ................................... 422/94

Primary Examiner—Robert J. Warden
Assistant Examiner—Theresa A. Trembley

[57] ABSTRACT

A catalytic combustion type CO gas sensor which is composed of an electrical circuit by serially arranging two coils composing an active section and a compensating section, and by providing serial bridge resistances, $r_1$ and $r_2$, opposing to the said coils, respectively, and via a gas sensitometer, and which determines the CO concentration based on the difference in value of resistance of both coils of the active section and the compensating section on catalytic combustion of CO, characterized by:

(A) that the values of the resistance of coils of the active section and the compensating section and bridge resistances, $r_1$ and $r_2$, at a definite temperature are made substantially the same, and thus the temperature coefficients of the coil of the active section and the bridge resistance $r_1$, and of the coil of the compensating section and the bridge resistance $r_2$ are made approximately the same.

(B) that the value of resistance of the coil of the active section at 150°–200° C., and the value of resistance of the coil of the compensating section at 80°–120° C. are made approximately the same, that, while a catalyst which is sensitive to both CO and $H_2$ at 150°–200° C. is baked on the coil of the active section, another catalyst which is sensitive to $H_2$ at 80°–120° C. is baked on the coil of the compensating section.

2 Claims, 4 Drawing Sheets

CATALYTIC COMBUSTION TYPE CO GAS SENSOR

DETAILED DESCRIPTION OF THE INVENTION

1. Applicable Industrial Field of the Invention

The present invention relates to a catalytical combustion type CO gas sensor. It especially relates to a catalytical combustion type CO gas sensor which can remarkably improve the CO gas sensitivity by eliminating zero drift in the sensitometer and eliminating the influence of other gas components such as $H_2$.

2. Prior Arts

CO (carbon monoxide) is a colorless, tasteless, odorless gas, and somewhat lighter than air (specific weight 0.967 when air is 1.000). However, it is very toxic, and it is said that a 1-2 hour inhalation of even 200 ppm causes headache, and an about 2 hour inhalation of 1,600 ppm is lethal. CO is generated often when high polymeric organic materials burn, for example, when incomplete combustion takes place in domestic equipments such as a gas water heater, bath heater, gas stove, oil stove, room heater and briquette burning. Resulting CO poisoning accidents occur frequently. About 60-80% of deaths from fire is said to be caused by CO poisoning, constituting a serious social problem.

Various types of CO alarms have been utilized in various countries, and various studies on them have been disclosed. However, it is not too much to say that there are few CO alarms which satisfies requirements of easy handling, reasonable cost, and high reliability.

The gas chromatographic technique may give most reliable means to determine the CO gas concentration. This technique compares the absorption spectrum of a gas to be detected with that of a reference gas. It yields very accurate measured values, and can detect even a very small amount of gas precisely. However, it was difficult to be utilized widely as a general purpose means because such gas chromatographic devices were very large in size, very expensive, and very complicated in technical handling. For this reason, it has eagerly desired to develop a more inexpensive and highly reliable CO sensor based on a novel principle.

CO sensors disclosed so far are roughly classified into the following groups:

a. $SnO_2$-type semiconductor sensors,
b. solid electrolyte sensors, and
c. electrolytic sensors.

Among them, (i) an $SnO_2$ semiconductor sensor has a principal drawback of inferior CO selectivity. To resolve this problem, several means have been tried, including introduction of OH groups, doping of Pd, Pt or the like to make it react with CO at 140°-150° C., and elimination of sensitivities to $H_2$, $H_2O$, $C_2H_5OH$ and the like with use of an activated carbon filter. However, these means have not still succeeded in resolving the problem. In addition, because the CO sensitivity of such a sensor was significantly affected by temperature and humidity during aging, leading to a poor reliability for a long time period. For these reasons, the $SnO_2$ type semiconductor sensor could not be evaluated as a suitable CO sensor.

(ii) A solid electrolyte sensor should be regarded as an application of zirconia ($ZrO_2$) oxygen sensor. However, it was not suitable for actual uses because it had problems in the use of a platinum membrane electrode and the peeling of the platinum membrane, and because its CO sensitivity was severely affected by gases other than CO.

Finally, (iii) an electrolytic sensor is based on absorption of CO in an electrolytic solution. When CO gas is absorbed in the electrolytic solution, and oxidized at an electrode which is placed in the solution, an electric current flows in proportion with the CO concentration. Because gases such as $H_2$, NO, and $C_2H_5OH$ which are present with CO, also are readily oxidized by the electrolytic solution, its gas selectivity is extremely poor. It has also a problem that the measured value is readily dependent on the absorption temperature of the electrolytic solution. Efforts to avoid such problems often necessitated replacement of the electrolytic solution, resulting a very troublesome operation.

The inventor paid attention to the catalytic combustion type sensor which would be most promising as a CO sensor long ago. He was engaged in development and improvement of catalytic combustion type sensors since a dozen or more years ago from viewpoints that they were remarkably superior to other type ones in their stability, preciseness, and reproductivity, and especially could well detect even very low concentrations of CO. The inventor succeeded especially in applying platinum or its alloy as the coil employed in the active section of the sensor, and in suitably applying $Al_2O_3$, a very good heat conductor, as an insulating material for the coil and a carrier for the catalyst. And, he made it possible to increase the surface area of the catalyst more than two times the conventional area by changing the form of the $Al_2O_3$ coating from the massive or bead type to the smooth electrodeposited type in order to make the catalyst adhere uniformly even on the inner sides of the coil. Thus, he succeeded in increasing the gas sensitivity more than 6 times by changing the diameter of the coiled wire from conventional 40 $\mu$m to 15-20 $\mu$m, and thus increasing the voltage impressible into the circuit from conventional 2 V to 6-12 V. In addition, he had resolved various problems concerning adjustment of the optimal temperature for the catalytic combustion of CO to be detected, synthesis of catalyst having excellent CO sensitivity, or improvement of the selectivity excluding gases other than CO. However, further problems had remained unresolved concerning elimination of zero drift on the output of the sensitometer, and removing of sensitivities to other gases without decreasing the sensitivity to CO.

PROBLEMS TO BE RESOLVED BY THE INVENTION

The invention was made in the background above-mentioned. It intends to resolve problems above-mentioned, concerning elimination of zero drift and removing of the influence of other gases such as $H_2$ and $C_2H_5OH$ without decreasing the CO sensitivity in the catalytic combustion type CO gas sensor.

Alarms for LP and for leakage of town gas generally work at relatively high gas concentrations, and are applied in relatively wide ranges of concentration. In these cases, some extent of zero drift may be often allowable. However, a CO gas alarming equipment necessitates a supersensitive sensor which works even against very low concentrations of CO. In this case, any zero drift caused by the sensor itself or by outside conditions must be eliminated as far as possible.

The zero drift in the invention means the phenomenon that, when, the zero point of the value of gas sensitivity which was adjusted to $V_o=0$ in a gas-free state shifts to the plus or minus side of the standard value due to outer conditions, especially due to the ambient temperature, or due to the aging progress. In other words, it means the phenomenon of fluctuation of the zero balance.

The sensor of the invention determines the CO concentration whereby CO to be detected is burned on the catalyst on the active section, that the generated heat is conducted to the coil, and that the change in resistance caused by the difference of temperature from the temperature of the coil of the compensating section is converted to the output of the sensitometer. In this case it is always essential that both coils of the active section and the compensating section are under the same environmental conditions.

When the active section is not blown by wind but the compensating section is blown, then the only compensating section is cooled, yielding a difference in surface temperature between both section. In this case, an output is generated at the plus side of the true output. On the contrary, when the active section is blown but the compensating section is not blown, such an output is generated at the minus side of the true output. Anyway, such a difference produces error in determination of output. Usually, as the CO concentration fluctuates by 100 ppm or so, the temperature at the coil of the active section rises or falls by 0.5° C. or so. Such a wind or air convection often acts on the coil, causing zero drift.

Consequently, in the case of a high-performance CO gas sensor, in which the CO concentration to be detected is set to 200 ppm at least, the alarm buzzer will go when the zero point is drifted to the plus side. On the contrary, the alarm buzzer will not go when the zero point is drifted to the minus side even though the gas concentration reaches the specified level. Thus, such a sensor is quite unsuitable as a CO sensor.

Such a zero drift as above mentioned is brought about not only by wind or other external conditions but also by the existence of a difference in heat radiation coefficient of coils between the active section and the compensating section. Although both coils are made in the same shape and size, a difference in heat radiation coefficient is brought about between them since a catalyst which responds to CO is coated on the coil of the active section.

In addition, such a zero drift is brought about even by a slight change in the bridge voltage $V_i$ of the dc source which is for submitting CO gas to catalytic combustion on the catalyst. For example, when, after adjusting $V_o$ to 0 at $V_i=6$, $V_i$ changes to 5.5, an output of $V=+0.8$ mV is produced. On the other hand, when $V_i$ changes to 6.5 V, another output of $V_o=-1.0$ mV is produced. Such a change of $V_i$ corresponds to the change of the ambient temperature; the change above-mentioned (6 $V\pm0.5$ V) corresponds to the change (about $\pm15°$ C.) in the ambient temperature. Thus, such a zero drift as above mentioned is often brought about also by any change in the ambient temperature, bridge voltage, or other external conditions.

The present invention intends to present a means appropriate for eliminating such a zero drift.

Next, a description is given on another problem to be resolved by the invention. That relates to the error of the CO sensitivity caused by the influence of the other gases.

So far there has been no countermeasure especially effective against a reduction of accuracy of CO sensitivity caused by overlap of sensitivities to CO and other gases, especially $H_2$.

As for countermeasures to eliminate the influence of other gases on the sensor, there are expected two possible ways—chemical means concerning the catalyst to be coated on the active section, and physical means to reconsider each component of the circuit.

The inventor carefully examined several hundred single and mixed catalytic systems possibly useful for CO detection. However, few systems were found which satisfied such requirements as follows. That is, (i) first such a system should have a good CO sensitivity, and should well detect even 200 ppm CO. Second, it should be very stable with little change during aging, and should hardly be reduced even in $H_2$ atmosphere. Third, it should hardly be sensitive to other gases such as $H_2$ and $C_2H_5OH$, which would be present with CO.

For example, so-called HOPCALIKE-type catalyst (a mixture of $MnO_2$, $CuO$, $NiO$ and $Ag_2O$), which is considerably reputable as a CO sensor, is little sensitive to $H_2$ and $C_2H_5OH$ with a CO sensitivity of 6-8 mV to 500 ppm CO. However, it has only a poor reliability as a CO sensor because of its serious drawback that its sensitivity as a CO sensor falls down rapidly within a relative short period of aging.

The invention presents a catalytic system which is affected little by other gases and sustains a high CO sensitivity during aging. Furthermore, the invention presents a means to secure an exact CO sensitivity with elimination of the influence of other gases by a combination of the temperature of sensor and the properties of catalyst.

Finally, the invention presents specified hoods and filters. Such hoods serve to exclude wind and convection of air which would considerably affect zero drift in the CO sensor. Such filters serve to prevent contact of other gases such as $H_2$ and $C_2H_5OH$ which would undesirably affect the CO sensitivity.

MEANS TO RESOLVE PROBLEMS

The catalytic combustion type CO sensor of the invention is composed of an electrical circuit by arranging both coils in series composing the active section and the compensating section, and by providing serial bridge resistances, $r_1$ and $r_2$, opposing to the said coils, respectively, and via a gas sensitometer, and determines the CO concentration based on the difference in value of resistance of both coils of the active section and the compensating section on catalytic combustion of CO, and, in addition, meets the following conditions, (A) to (D).

(A) The zero drift in the sensor is dissolved whereby, the value of resistance of the coil of the compensating section in a gas-free state and at a definite temperature around ordinary temperatures is made somewhat larger than that of the coil of the active section, and that a trimming resistance is incorporated into the circuit parallell to the coil of the compensating section.

(B) The zero drift is eliminated whereby both coils of the active section and the compensating section exhibit the same value of resistance in a gas-free state and at a definite temperature around ordinary temperatures, that the bridge resistances, $r_1$ and $r_2$, have the same value of resistance in the gas-free state and at the definite temperature, and that temperature coefficients of the coil of the active section and of the bridge resistance $r_1$, and temperature coefficients of the coil of the compensating section and the bridge resistance $r_2$ are made approximately the same, respectively.

(C) The influence of other gases on the CO sensitivity is eliminated by a mixed catalytic system which is constituted by adding a CuO-containing co-catalyst to the noble metal catalyst, which is fixed to the surface of the coil of the active section by less than a half of the noble metal catalyst.

(D) The value of resistance of the coil of the active section in the gas-free state and at 150°–200° C., and the value of resistance of the coil of the compensating section in the gas-free state and at 80°–120° C. are set to approximately the same; while a catalyst which is sensitive to both CO and $H_2$ at 150°–200° C. is baked on the coil of the active section, another catalyst which is sensitive to $H_2$ at 80°–120° C. is baked on the coil of the compensating section; and the $H_2$ sensitivity which corresponds to the $H_2$ concentration measured at the compensating section is subtracted from the sum of sensitivities to CO and $H_2$ at the active section to eliminate the influence of gases other gases such as $H_2$.

Figure 1:
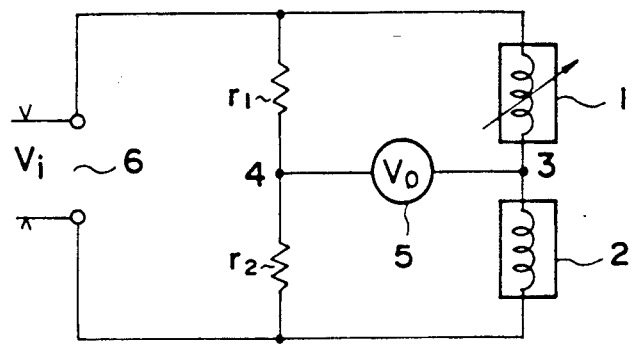
FIG. 1 shows the circuit diagram of a catalytic combustion type CO sensor of the invention.

Numbers or marks in the drawings represent the following matters, respectively. 1: active section, 2: compensating section, $r_1$ and $r_2$: resistance, 5: sensitometer, 6: bridge power source, 7: trimming resistance, 8: stainless steel wire cap, 9: special cap, 11: filter, 13: surrounding part, 14 and 15: network part, and 16: particles.

DESCRIPTION OF THE PREFERRED EMBODIMENT

The present invention is further described based on an example, referring to the drawings as follows.

As shown in FIG. 1, the CO gas sensor of the invention is constituted by having serially arranged active section 1 and compensating section 2; serially arranging bridge resistances $r_1$ and $r_2$ on opposite sides of sections 1 and 2, parallelly; providing a sensitometer 5, which displays voltage (mV), between the midpoint 3 between the active section 1, and the compensating section 2, and the midpoint 4 between the bridge resistances $r_1$ and $r_2$; and providing a bridge power source 6 which impresses direct current to the active section 1, compensating section 2, and bridge resistances $r_1$ and $r_2$.

The active section 1, and the compensating section 2 have the same volume and size. Their main part consists of a 40 or more turned coil of 15–20 μm diameter wire of platinum (Pt) or platinum alloy such as Pt-W, Pt-Ni, and Pt-Rt, which has a relatively large temperature coefficient and is chemically stable. And an insulating film of good heat conductive material such as $Al_2O_3$ is fixed on the surface of the coil of the active section 1.

As for $Al_2O_3$, it is not desirable to be fixed in the form of mass or beads, but in the form of electrodeposited film, and it is desirable to attach onto the upper surface of the coil also. Onto the upper surface of the $Al_2O_3$ layer, a catalyst such as palladium oxide layer, by which CO gas to be detected is selectively contact burned is lamellarly attached. The compensating or dummy section is constituted by the same coil as that for the active section, but is not provided with any insulating film, unlike the active section, or any catalytic layer which is sensitive to CO. As the bridge power source, 6 V direct current is usually used.

The gas sensitivity, $\Delta V$, of the gas sensor of the invention is given by the following formula:

$$\Delta V = \frac{\Delta R}{4R} \cdot Vi$$

$$\Delta R = \alpha \cdot a \cdot m \cdot Q/C,$$

where $\Delta V$ is the gas sensitivity in mV; $\Delta R$ the change in the resistance of the coil by the CO gas combustion; R the value of resistance of the coil; Vi the bridge voltage; $\alpha$ a constant; a the temperature coefficient of the wire material of the coil; m the concentration of CO gas; Q the molecular combustion heat of CO; and C the heat capacity of the sensor.

The sensor thus constituted deteriorates little time-dependently, and is relatively good in its gas selectivity with a high sensitivity. It can detect well even a low concentration of CO especially when 6 V direct current is employed as the bridge voltage Vi and the gas combustion temperature is set to 150° C. to 220° C.

However, even such a sensor constituted as above has still had problems to be resolved.

Figure 2:
FIG. 2 illustrates the zero drift.

First, it has had a problem of zero drift insensitivity. In the first place, it is desirable that the active section and the compensating section exhibit the substantially same properties regardless of some change in ambient temperature. Actually, however, zero drift is generated as shown in FIG. 2, caused by little difference in pitch interval and in radiating coefficient of both coils, a local change in temperature of coils by wind or air flow, fluctuation of the bridge voltage, or the like.

Figure 3:
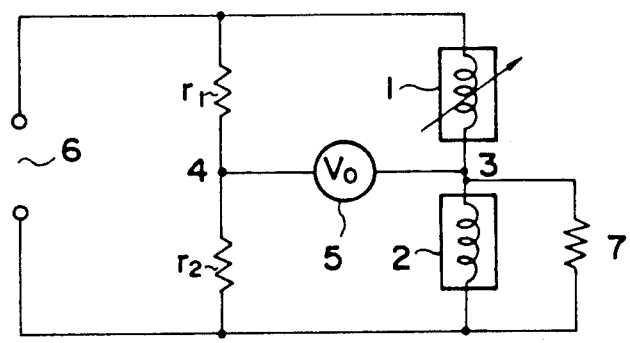
FIG. 3 shows the circuit diagram of the catalytic combustion type CO sensor shown in FIG. 2 to which a trimming resistance was incorporated.

In order to resolve such a problem of zero drift, the following means is presented in the invention. That is, the invention intends to resolve the problem of zero drift by setting the coil resistance of the compensating section 2 to a value somewhat larger than the coil resistance of the active section 1 at the same temperature as a definite temperature (for example, 25° C.) around ordinary temperatures and in a gas-free state, incorporating the trimming resistance 7 parallel to the coil of the compensating section 2 as shown in FIG. 3, and then making the coil resistances of the active section 1 and the compensating section 2 at the definite temperature (for example, 25° C.) around ordinary temperature the substantially same level.

More concretely, the coil resistances of the active section 1 and the compensating section 2 of such a sensor are shown in Table 1, for example.

TABLE 1

| Coil | Ambient temp. | | |
|---|---|---|---|
| | 0° C. | 25° C. | 50° C. |
| Active section | 63.72Ω | 65.91Ω | 67.37Ω |
| Compensating section | 65.65Ω | 67.89Ω | 69.32Ω |

In order to make the both coil resistances the same at 25° C., the trimming resistance 7 is incorporated parallel to the coil of the compensating section. The value Tr of the incorporated trimming resistance are as follows:

$$Tr = \frac{67.86 \times 65.91}{67.86 - 65.91} = 2293 \, (\Omega) \quad (1)$$

By thus incorporating this trimming resistance, combined resistances at other ambient temperatures fall as follows:

$$0° C.: \frac{65.65 \times 2293}{65.65 + 2293} = 63.82 \, (\Omega) \quad (2)$$

$$50° C.: \frac{69.32 \times 2293}{69.32 + 2293} = 67.28 \, (\Omega) \quad (3)$$

Thus in the present invention, the combined resistance $R_3$ of the compensating section, which is calculated by the following formula:

$$R_3 = \frac{R_2 \times R_1}{R_2 + Tr}, \quad (4)$$

is made the substantially same as the resistance $R_1$ of the active section by setting the coil resistance $R_2$ of the compensating section at a definite temperature around ordinary temperatures somewhat larger than the coil resistance $R_1$ of the active section at the same temperature and then incorporating the trimming resistance 7 of resistance Tr parallel to the coil of the compensating section 2.

Resistances of the active section and the compensating section at 0° C., 25° C., and 50° C. are summarized as shown in Table 2.

TABLE 2

| Coil | Ambient temp. | | |
|---|---|---|---|
| | 0° C. | 25° C. | 50° C. |
| Active section | 63.72Ω | 65.91Ω | 67.37Ω |
| Compensating section | 63.82Ω | 65.91Ω | 67.28Ω |

Figure 4:
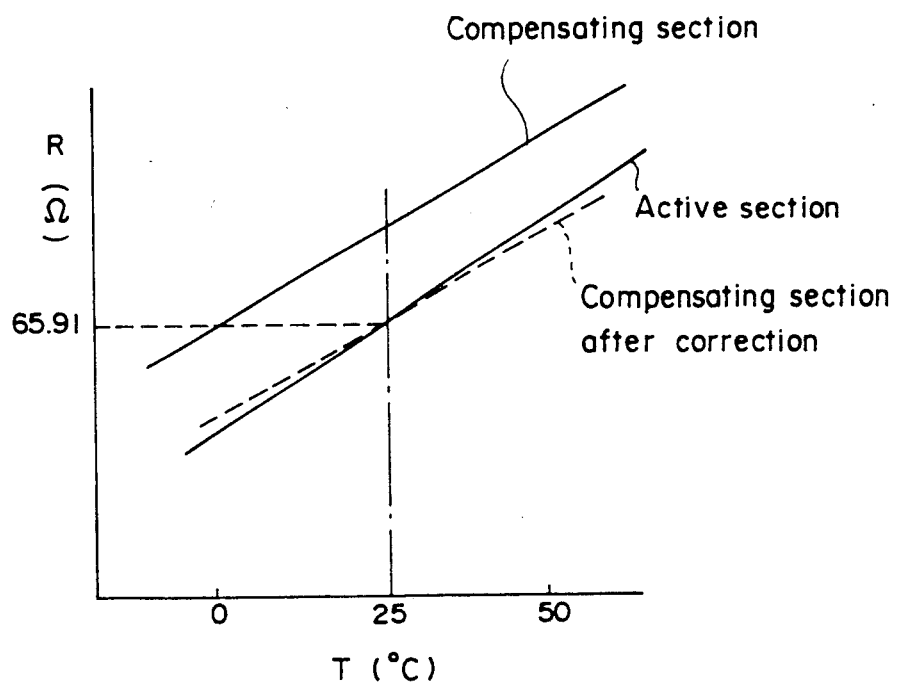
FIG. 4 shows the resistance-temperature (R-T) characteristic diagram of the circuit after the incorporation of the trimming resistance.
Figure 5:
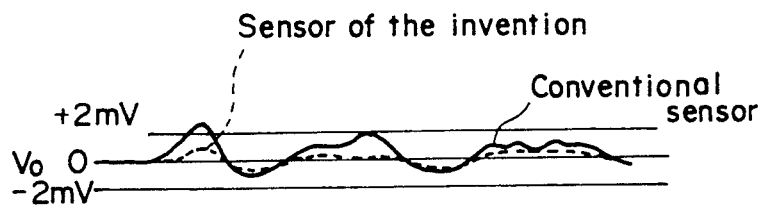
FIG. 5 illustrates the zero drift improved by the incorporation of the trimming resistance.

The result of Table 2 is graphically shown by FIG. 4. Temperature (T) - resistance (R) properties in the active section (S) and the compensating section (D) are adjusted so as to overlap almost completely, and, consequently, the zero drift is largely eliminated. In FIG. 5, the broken line shows the zero drift thus improved by incorporating the trimming resistance.

Furthermore, the invention presents a more effective means to resolve the problem of zero drift as follows.

That is, in addition to the means by which the coil resistances of the active section and the compensating section at a definite temperature (for example, 25° C.) around ordinary temperatures made the substantially same, the other means intends to further effectively eliminate the zero drift in the CO sensitivity by setting temperature coefficients (hereinafter called TCR) of the coil of the active section and the bridge resistance $r_1$ at a range of ambient temperature (for example, 0° C. to 50° C.), and TCR of the compensating coil and bridge resistance $r_2$ to the almost same.

TCR in the present specification are calculated with the following formula:

$$(r_{max}-r_{min})/r_{min}(t_{max}-t_{min}) \quad (5)$$

where $r_{max}$ is the value of resistance at the maximum ambient temperature; $r_{min}$ the value of resistance at the minimum ambient temperature; $t_{max}$ the maximum ambient temperature; and $t_{min}$ the minimum ambient temperature. TCR of the coils of the active section and the compensating section shown in Table 2 at ambient temperatures ranging from 0° C. to 50° C. are given as follows:

$$TCR \text{ (active section)} = \quad (6)$$

$$\frac{67.37 - 63.72}{63.72} /(50-0) = 1,145 \text{ (ppm/°C.)}$$

$$TCR \text{ (compensating section)} = \quad (7)$$

$$\frac{67.28 - 63.82}{63.82} /(50-0) = 1,084 \text{ (ppm/°C.)}$$

Further, when, as mentioned above, resistances having values of 330Ω at 25° C. are employed as $r_1$ and $r_2$, and the TCRs of $r_1$ and $r_2$ are 1,145 ppm/°C. and 1,084 ppm/°C., respectively, for $r_1$, the values at 320Ω and 339Ω are applicable at 0° C. and 50° C., respectively; and for $r_2$, the values of 321Ω and 338Ω applicable at 0° C. and 50° C., respectively. Modification of resistances $r_1$ and $r_2$ to those having TCR mentioned above is readily possible by a well-known spattering or electroless plating method.

Figure 6:
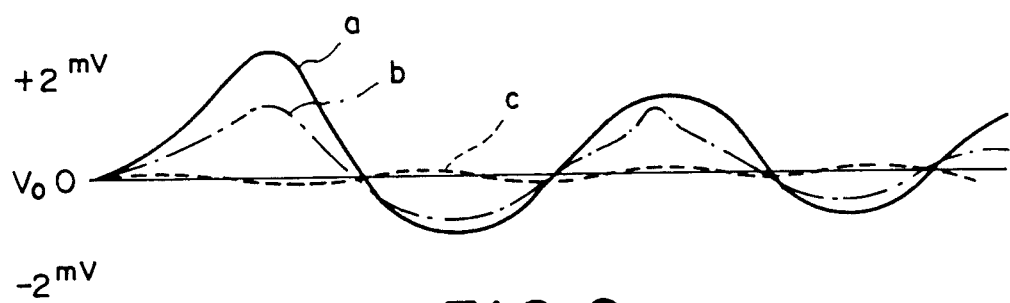
FIG. 6 illustrates comparison of zero drifts.

FIG. 6 illustrates an example of zero drift by a gas sensitometer based on the invention. It shows that, comparing with the zero drift (Curve a) in the untreated case, the zero drift (Curve b) in the case in which the value of resistance is modified by incorporating the trimming resistance into the compensating section is obviously improved, and that the zero drift in the case in which bridge resistances ($r_1$ and $r_2$) are employed is very effective in the elimination of zero drift (Curve C).

Figure 7I:
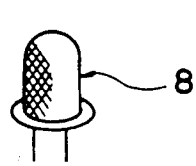
FIG. 7 (i) and (ii) show the conventional cap and the cap of the invention, respectively.

As for improvement of zero drift, it is effective to apply special caps which cover the coils of the active section and the compensating section in order to eliminate the influence on the sensor. In the sensor of the invention, every about 100 ppm rise of CO concentration causes an about 0.5° C. rise of temperature of the coil. Using a conventional cap 8 made of about 100-mesh stainless steel gauze as shown in FIG. 7(i), it is difficult to accurately measure the CO concentration because of generation of zero drift due to the influence of air convection or wind. In the invention, a cap made of double gauze is employed so that the space between both gauzes may diffuse the wind which comes from the outside, resulting in a remarkable effect of elimination of zero drift.

Figure 7:
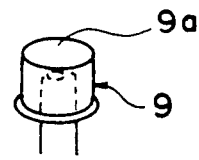
Figure 8:
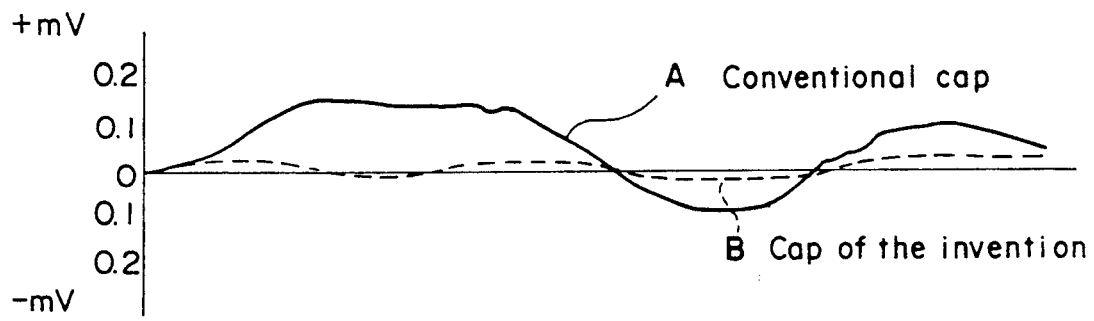
FIG. 8 illustrates comparison of zero drifts of the conventional sensor and the sensor of the invention.

Furthermore in the invention, a special cap 9 is employed as shown in FIG. 7(ii). The upper part of the cap 9 is covered with a lid 9a made of metal or glass fiber, and the side wall of the cylindrical cap 9 prevents the influence of air flow or wind from the side. In the CO sensor of the invention, the use of such a cap is particularly effective since gas concentrations (for example 100 ppm) much lower than the lower explosion limit (L.E.L.) should be determined. Curves A and B in FIG. 8 show the progress of zero drift when a conventional cap and a cap of the invention are employed, respectively.

The other purpose of the invention is to remove the sensitivity of other gases such as $H_2$ and $C_2H_5OH$ without any reduction in the sensitivity of CO in the sensor having a circuit shown in FIG. 1. For this purpose, the catalyst used in the active section 1 contains CuO as an essential co-catalytic component besides a catalytic component of noble metals such as Pt-black and/or PdO, and further contains one or two other metal oxides such as ZnO, CdO and $MnO_2$. Then, the content of CuO should be less than a half of the noble metal catalytic component.

Since CuO is readily reduced by hydrogen in its single use, other metal oxides such as ZnO, CdO and $MnO_2$ are added to prevent the reduction of CuO. The reason for limiting the amount of the co-catalyst to less than the amount of the noble metal catalyst is because of the prevention of the reduction of CO sensitivity due to the presence of other oxides.

In the example, 20 $\mu$m Pt wire of higher than 99.9% purity was used. The wire was wound at a winding diameter of 0.8 $\phi$ with almost uniform pitch intervals, and exhibited a resistance of $40\Omega \pm 0.5$ $\Omega$ at 25° C. It was welded to the stem, and used in the active section and the compensating section. The wound coil was gently rinsed, dried, and then adhered with $Al_2O_3$ electrodepositionally to form a cylinder. $Al_2O_3$ was well sintered by resistance heating. Then, a mixed solution having a composition shown in Table 3 was collected by a pipet, and dropwise added onto the upper surface of $Al_2O_3$. After air drying, the impregnated coating was decomposed by resistance heating at 500°–600° C. Thus a coil provided with a Pt-black-CuO-ZnO catalytic system was obtained.

TABLE 3

Aqueous solution (1:10) of $H_2PtCl_6.6H_2O$
Aqueous solution (1:20) of $Cu(NO_3)_2.3H_2O$
Aqueous solution (1:20) of $Zn(NO_3)_2.4H_2O$ Then, the coil was impregnated with an aqueous solution (1:20) of $Cd(NO_3)_2 \cdot 6H_2O$, and decomposed by resistance heating to form a CdO composition which had a heat radiation coefficient comparable to the active section and was gas-nonsensitive in order to use in the compensating section. For such a coil of the compensating section, in addition, it is desirable that such a CdO composition contains a trace amount of CuO and $CrO_3$ for the purpose of eliminating the influence of the remaining trace of $C_2H_5OH$.

Then, the coil was well rinsed with pure water until no $Cl^-$ ions were detected, dried, and then was submitted to a resistance aging treatment to make the catalyst disperse uniformly. The sensor of the invention was completed by providing the specified cap.

Table 4 shows measured values of CO sensitivity (Vo) of a sensor constituted by both the active section for which the Pt-black-CuO-ZnO catalyst above-mentioned is applied, and the compensating section for which the CdO above-mentioned is applied, under a condition of CO 500 ppm, $H_2$ 500 ppm, and $C_2H_5OH$ 1,000 ppm. In this case, the gas combustion temperature at the active section was about 205° C. since a DC 6 V current was impressed.

TABLE 4

| Sample No. | CO 500 ppm | $H_2$ 500 ppm | $C_2H_5OH$ 1000 ppm |
|---|---|---|---|
| 1 | 6.3 mV | 0.4 mV | 0.1 mV |
| 2 | 6.1 mV | 0.6 mV | 0.2 mV |
| 3 | 7.0 mV | 0.8 mV | 0.1 mV |
| 4 | 5.9 mV | 0.4 mV | 0.1 mV |
| 5 | 6.5 mV | 0.6 mV | 0.2 mV |

According to Table 4, while Vo comes to 2.5–2.8 mV as the CO concentration comes to 200 ppm, Vo comes to 0.4–0.8 mV and 0.1–0.2 mV only as the $H_2$ and $C_2H_5OH$ concentrations come to 500 ppm and 1,000 ppm, respectively. Therefore, such a sensor is useful surely without giving misinformation when it is incorporated into an incomplete combustion alarm of a domestic combustion system, or a domestic fire alarm.

Figure 9:
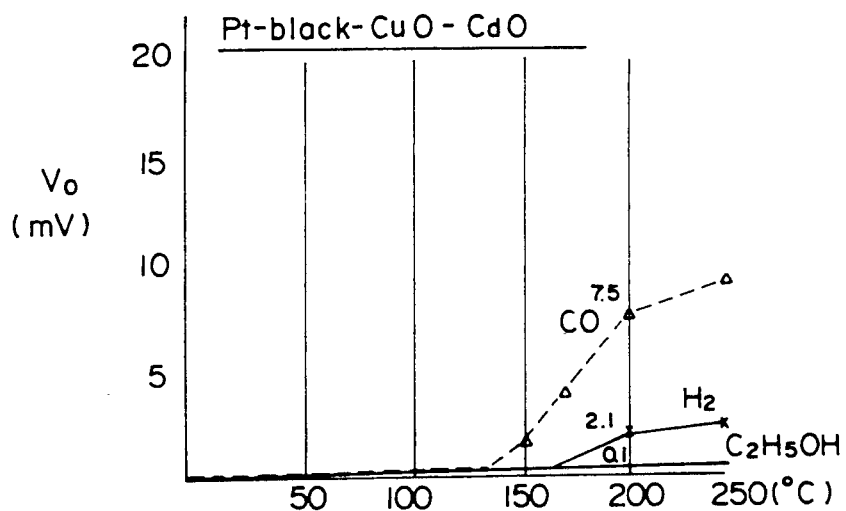
FIG. 9 illustrates the relation between the CO, $H_2$ and $C_2H_5OH$ sensitivities and the catalytic combustion temperature in a Pt-black-CuO-CdO type catalyst.

As shown in FIG. 9, using a Pt-black-CuO-CdO catalytic system, the sensitivity output Vo is 7.5 mV for a CO concentration of 500 ppm, while it is 2.1 mV and 0.1 mV only for $H_2$ and $C_2H_5OH$ concentrations of 500 ppm and 1,000 ppm, respectively, at a combustion temperature of 200° C. Thus it has been found that the $H_2$ and $C_2H_5OH$ sensitivities are removed more effectively.

For a catalytic system of the invention, any of PdO-CuO-ZnO, PdO-CuO-CdO, PdO-Pt-black-CuO-ZnO, and PdO-Pt-black-CuO-CdO systems is suitable besides Pt-black-CuO-ZnO and Pt-black-CuO-CdO systems above-mentioned.

Figure 10:
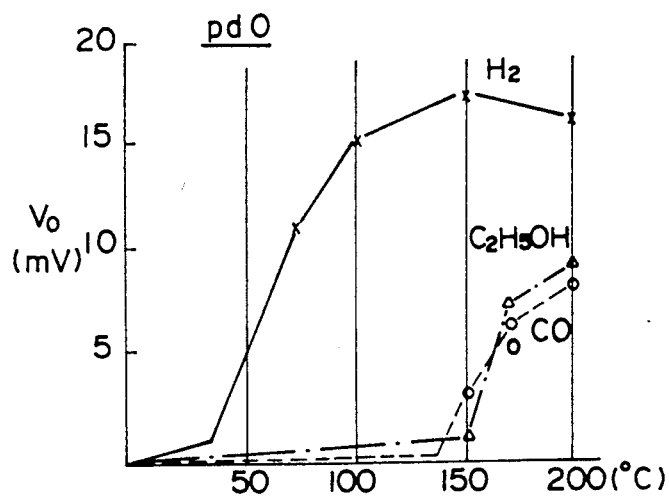
FIGS. 10 and 11 illustrate the relation between the sensitivity and the catalytic combustion temperature in catalysts composed of PdO and Pt-black alone, respectively.
Figure 11:
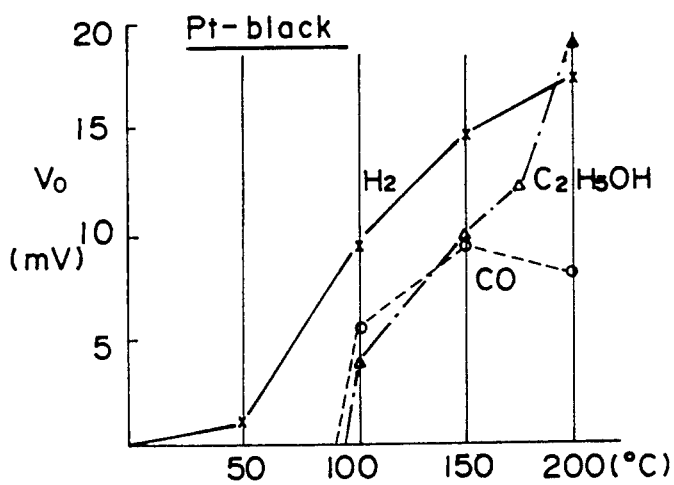

FIGS. 10 and 11 show results of PdO and Pt-black alone without any co-catalyst, respectively. They involve a large possibility to yield misinformation on determining the CO concentration because of larger $H_2$ and $C_2H_5OH$ sensitivity even when the CO concentration is similar to that in the case of FIG. 10.

Next, a description is given on a filter which covers the upper part of the sensor for the purpose of removing $H_2$ and $C_2H_5OH$ sensitivities.

Figure 12:
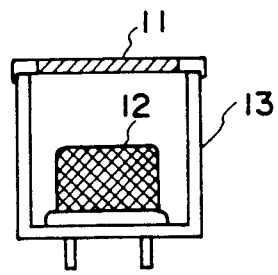
FIGS. 12 and 13 illustrate filters of the invention.
Figure 13:
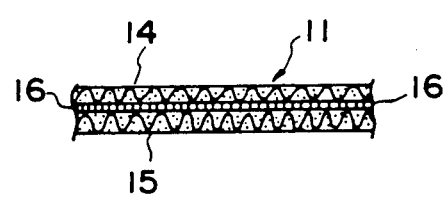

As shown in FIG. 12, such a filter 11 is placed at the top hole of a vinyl surrounding part 13 which surrounds the sensor covered with the cap 12. As shown in FIG. 13, the filter 11 is composed of laminated networks (2 pieces in the example), 14 and 15. One or more kinds of ZnO and $TiO_2$ particles 16 are filled between the networks.

These particles catalytically oxidize or decompose $H_2$ or $C_2H_5OH$. For example, $TiO_2$ oxidizes $H_2$ to $H_2O$, and then the reduced $Ti_2O_3$ returns to the state of $TiO_2$, which, in turn, oxidizes $H_2$ again as follows:

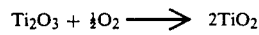

ZnO also follows a similar mechanism. Metallic palladium serves as a catalyst which ionizes $O_2$ in air, and oxidizes $H_2O$. Unlike such a material as activated carbon serving only as an adsorbing agent, these material can be permanently used to remove $H_2$, $C_2H_5OH$ and the like.

Next, a description is given on the means to physically eliminate the influence of other gases such as $H_2$ and $C_2H_5OH$, which affect the CO sensitivity.

According to the invention, the CO sensitivity is obtained by that, when bridge voltage is impressed in the active section and the compensating section, the surface temperature of both sections are brought to 150°–200° C. and 80°–120° C., respectively, and, when the current is conducted, the resistances of the respective whole coils are set to approximately the same, that a catalyst which is sensitive to both CO and $H_2$ at 150°–200° C. is baked on the coil of the active section, while another catalyst which is sensitive to $H_2$ at 80°–120° C. is baked on the coil of the compensating section, and that the $H_2$ sensitivity at the active section, which corresponds to the $H_2$ concentration measured by the compensating section, is subtracted from the sum of CO and $H_2$ sensitivities at the active section.

The active section is provided with the following catalyst, and exhibits the following value of sensitivity under the condition of CO concentration of 500 ppm and temperature of 200° C.:

$MnO_2$-ZnO-CuO catalyst: 5.1 mV, or
$MnO_2$-CuO-PdO catalyst: 6.8 mV.

This active section exhibits the following value of sensitivity under the condition of $H_2$ concentration of 500 ppm and temperature of 200° C.:

$MnO_2$-ZnO-CuO catalyst 2.4 mV, or
$MnO_2$-CuO-PdO catalyst: 4.2 mV.

On the other hand, the compensating section is provided with a PdO catalyst, and exhibits a sensitivity of 9.4 mV under the condition of $H_2$ concentration of 500 ppm and temperature of 100° C. The compensating section does not exhibit any sensitivity under the condition of CO concentration of 500 ppm and temperature of 100° C. at all.

That is, a current of 9.4 mV is outputted at the compensating section under the condition of $H_2$ concentration of 500 ppm and temperature of 100° C. Therefore, if the outputted value of $H_2$ sensitivity of the tested gas at 100° C. at the compensating section is 1.88 mV, for example, the $H_2$ concentration, B, is calculated as B=100 (ppm) from 9.4:1.88=500:B, and it is found that the atmosphere surrounding the sensor contains 100 ppm $H_2$.

Consequently, concerning an active section which is provided with a $MnO_2$-ZnO-CuO catalyst, for example: the $H_2$ sensitivity, A, is calculated as A=0.48 mV form 2.4:A=500:100, and, when the sum of sensitivities is 6.58 mV, the CO sensitivity is obtained as 6.58−0.48=6.1 (mV), and, the corresponding CO concentration is determined as 500 ppm.

In these ways, the sensor of the present invention secures a substantial CO sensitivity, in view of the present situation that there are few catalysts nonsensitive to $H_2$ but well sensitive to CO, by that the compensating section is provided with a catalyst such as PdO, which is nonsensitive to CO but well sensitive to $H_2$ around 100° C., while the active section is provided with a catalyst such as $MnO_2$-ZnO-CuO, which is well sensitive to CO and sensitive also to $H_2$ around 200° C., and then the sum of sensitivities is calculated as follows:

[sum of CO and $H_2$ senstivities] −

[$H_2$ sensitivity] = [CO sensitivity]

EFFECTS OF THE INVENTION

The present invention is constituted as above described, and presents a very useful sensor applicable to gas alarms and the like by remarkably improving the CO gas sensitivity of catalytic combustion type CO sensors through resolving traditional problems of (i) zero drift, and (ii) influence of other gas components, and especially make it possible to detect lower concentrations of CO.

What is claimed is:

1. A catalytic combustion type CO gas sensor comprising:
   an electrical circuit including two coils arranged in series defining a active section and an compensation section respectively,
   resistances, $r_1$ and $r_2$, arranged in series opposing said coils respectively,
   a gas sensitometer bridging the junction between said coils and said resistances which determines CO concentration based on the difference in resistance of said coils on catalytic combustion of CO,
   said coils having substantially the same resistance in gas-free state at a definite temperature around 25° C.,
   said resistances $r_1$ and $r_2$ having substantially the same resistance in a gas-free state at a definite temperature around 25° C.,
   the temperature coefficient of the active section coil and resistance $r_1$ being approximately the same, and
   the temperature coefficient of the compensating section coil C2 and resistance $r_2$ being approximately the same.

2. A catalytic combustion type CO gas sensor comprising:
   an electrical circuit including two coils arranged in series defining a active section and an compensation section respectively,
   resistances, $r_1$ and $r_2$, arranged in series opposing said coils respectively,
   a gas sensitometer bridging the junction between said coils and said resistances which determines CO concentration based on the difference in resistance of said coils on catalytic combustion of CO.,
   said resistance of coil the active section coil at 150°–200° C. in a gas-free state and the resistance of coil the compensating section coil at 80°–120° C. in a gas-free state are approximately the same,
   said coil the active section coil having baked thereon a catalyst which is sensitive to both CO and $H_2$ at 150°–200° C.,
   said coil the compensating section coil having baked thereon a catalyst which is sensitive to $H_2$ but not CO at 80°–120° C., and
   said gas sensor being arranged so that CO sensing thereby is obtained by subtracting the $H_2$ value sensed by said coil the compensating section coil from the sum of CO and $H_2$ values sensed by said coil the active section coil.

* * * * *